(12) United States Patent
Kim et al.

(10) Patent No.: US 9,850,223 B2
(45) Date of Patent: Dec. 26, 2017

(54) METAL CATALYSTS FOR SELECTIVE FORMATION OF CYCLIC CARBONATES, PROCESS FOR PREPARING CYCLIC CARBONATE USING THE SAME AND USE OF CYCLIC CARBONATE

(71) Applicant: KOREA ADVANCED INSTITUTE OF SCIENCE AND TECHNOLOGY, Daejeon (KR)

(72) Inventors: Hyunwoo Kim, Daejeon (KR); Yuseop Lee, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 0 days.

(21) Appl. No.: 15/207,906

(22) Filed: Jul. 12, 2016

(65) Prior Publication Data

US 2017/0081302 A1  Mar. 23, 2017

(30) Foreign Application Priority Data

Sep. 18, 2015  (KR) .......................... 10-2015-0132290

(51) Int. Cl.
| | |
|---|---|
| *C07D 317/44* | (2006.01) |
| *C07D 317/46* | (2006.01) |
| *C07D 317/70* | (2006.01) |
| *C07D 493/04* | (2006.01) |
| *B01J 31/22* | (2006.01) |

(52) U.S. Cl.
CPC ........ *C07D 317/44* (2013.01); *B01J 31/2295* (2013.01); *C07D 317/46* (2013.01); *C07D 317/70* (2013.01); *C07D 493/04* (2013.01); *B01J 2231/49* (2013.01); *B01J 2531/31* (2013.01); *B01J 2531/842* (2013.01)

(58) Field of Classification Search
CPC .. C07D 317/44; C07D 317/46; C07D 317/70; C07D 493/04; B01J 31/2295; B01J 2231/49; B01J 2531/31; B01J 2231/842
See application file for complete search history.

(56) References Cited

U.S. PATENT DOCUMENTS 4,931,571 A * 6/1990 Weinstein ............ C07D 301/02
549/230
5,283,356 A   2/1994 Marquis et al.

FOREIGN PATENT DOCUMENTS

| JP | 56-128778 | 10/1981 |
|---|---|---|
| JP | 59-13776 | 1/1984 |
| JP | 07-206547 | 8/1995 |
| KR | 10-2005-0115694 | 12/2005 |
| WO | 2005/003113 | 1/2005 |

OTHER PUBLICATIONS

North, Michael, et al., "Mechanism of Cyclic Carbonate Synthesis from Epoxides and CO2," Angew. Chem. Int. Ed. 2009, 48, 2946-2948, Wiley-VCH Verlag GmbH & Co. KGaA, Weinheim, <www.angewandte.org>.

Qin, Zengquan, et al., "Cobalt-Based Complexes for the Copolymerization of Propylene Oxide and CO2 : Active and Selective Catalysts for Polycarbonate Synthesis," Angew. Chem. Int. Ed. 2003, 42, 5484-5487, Wiley-VCH Verlag GmbH & Co. KGaA, Weinheim, <www.angewandte.org>.

Whiteoak, Christopher J., et al., "A Powerful Aluminum Catalyst for the Synthesis of Highly Functional Organic Carbonates," ACS Publications, American Chemical Society 2013, Am. Chem. Soc. 2013, 135, 1228-1231, Published: Jan. 10, 2013.

Whiteoak, Christopher J., et al., "Reactivity Control in Iron(III) Amino Triphenolate Complexes: Comparison of Monomeric and Dimeric Complexes," ACS Publications, American Chemical Society 2012, Inorg. Chem. 2012, 51, 10639-10649, Published: Sep. 24, 2012.

Laserna, Victor, et al., "Carbon Dioxide as a Protecting Group: Highly Efficient and Selective Catalytic Access to Cyclic cis-Diol Scaffolds," 2014 Wiley-VCH Verlag GmbH & Co. KGaA, Weinheim, Angew. Chem. Int. Ed. 2014, 53, 10416-10419, <www.angewandte.org>.

Orsini, Fulvia, et al., "Enantiopure vic-amino alcohols and vic-diamines from (1R,2S)-1,2-dihydroxy-1,2-dihydronaphthalene," Tetrahedron: Asymmetry 12 (2001) 2961-2969.

(Continued)

*Primary Examiner* — D M Seaman
(74) *Attorney, Agent, or Firm* — Hauptman Ham, LLP (57) ABSTRACT

Provided are a novel metal catalyst for preparing cyclic carbonate, and a method for preparing cyclic carbonate using the same, and more particularly, a method for selectively preparing cyclic carbonate in a high yield and at a higher conversion rate as compared to the existing catalysts, using the metal complex including a ligand represented by Chemical Formula 1 below and a trivalent metal in Group 8 or Group 13 as a catalyst and using various structures of epoxide compounds and carbon dioxide as raw materials. In addition, provided are the prepared cyclic carbonate, and an electrolyte including the same:

[Chemical Formula 1]

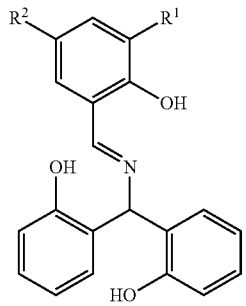

in Chemical Formula 1, $R^1$ is hydrogen, (C1-C20)alkyl or halogen; $R^2$ is hydrogen, (C1-C20)alkyl, (C1-C20)alkoxy, halogen or nitro.

11 Claims, 3 Drawing Sheets

(56) References Cited

OTHER PUBLICATIONS

Lee, Yuseop, et al., "Iron Catalyst for Selective Formation of Cyclic Carbonates form CO2 and Epoxides," Department of Chemistry, Korea Advanced Institute of Science and Technology, Daejeon, Republic of Korea.

Lee, Yuseop, et al., "Iron and Aluminum Catalysts for Selective Formation of Cyclic Carbonates from CO2 and Internal Epoxides," Department of Chemistry, Korea Advanced Institute of Science and Technology, Daejeon, Republic of Korea.

Darensbourg, Donald J. et al., "Mechanistic Aspects of the Copolymerization Reaction of Carbon Dioxide and Epoxides, Using a Chiral Salen Chromium Chloride Catalyst," JACS Articles, May 2002, J. Am. Chem. Soc. 2002, 124, 6335-6342.

Whiteoak, Christopher J., "Reactivity Control in Iron(III) Amino Triphenolate Complexes: Comparison of Monomeric and Dimeric Complexes," Institute of Chemical Research of Catalonia (ICIQ), Tarragona, Spain, ACS Publications, American Chemical Society, Sep. 24, 2012.

\* cited by examiner

METAL CATALYSTS FOR SELECTIVE FORMATION OF CYCLIC CARBONATES, PROCESS FOR PREPARING CYCLIC CARBONATE USING THE SAME AND USE OF CYCLIC CARBONATE

CROSS-REFERENCE TO RELATED APPLICATIONS

This application claims priority under 35 U.S.C. §119 to Korean Patent Application No. 10-2015-0132290, filed on Sep. 18, 2015, in the Korean Intellectual Property Office, the disclosure of which is incorporated herein by reference in its entirety.

TECHNICAL FIELD

The following disclosure relates to a catalyst for preparing cyclic carbonate, particularly, a catalyst used for selectively preparing cyclic carbonate by reacting an alkylene oxide compound with carbon dioxide, and a method for preparing cyclic carbonate using the same. In addition, the present invention relates to the prepared cyclic carbonate, and an electrolyte including the same.

BACKGROUND

The conversion of abundant and renewable $C_1$ source and carbon dioxide ($CO_2$) to commodity chemicals has received a lot of recent attention in part as a sustainable solution for carbon dioxide recycling and reduction. Particularly, reaction of carbon dioxide and epoxides to form polycarbonates or cyclic carbonate is considered as one of the promising industrial processes.

The cyclic carbonate is used as raw materials of polycarbonate, intermediates for cosmetics and pharmaceutical process, oxyalkylation agents in a dye synthesis process, protective agents of a process equipment, and solvents of a fiber production process. In addition, the cyclic carbonate may be used as an intermediate in preparing alkylene glycol from alkylene oxide. Recently, a range at which the cyclic carbonate is used has been continuously expanded to a solvent of a polymer electrolyte of a secondary battery, etc.

Several catalytic systems such as transition metal complexes or organocatalysts were reported to promote the reaction of carbon dioxide and alkylene oxide. As a well-known example, there are salen-based complexes (salen=N, N'-bis(salicylidiene)ethylenediamine) of Al, Cr, Mn, Co and Zn that are recognized to be effective for both polycarbonate and cyclic carbonate synthesis. [Cr(salen)] and [Co(salen)] complexes for polycarbonate synthesis were developed; meanwhile, binuclear [Al(salen)]$_2$O complex for selective cyclic carbonate synthesis was developed.

In addition to metal-dependent selectivity, research into ligand modification in a complex to improve reactivity and selectivity of a catalyst was conducted, and a highly active carbon dioxide/propylene oxide copolymerization catalyst prepared by incorporating co-catalyst ammonium salts in [Co(salen)] complexes has been reported, which is being developed for industrial production of polypropylene carbonate.

In addition, it has been reported that mononuclear Al complexes and dinuclear Fe complexes based on amino tris(phenolate) ligands have excellent reactivity and selectivity in the cyclic carbonate synthesis.

As other different methods, for example, Japanese Patent Laid-Open Publication No. S56-128778 discloses cyclic carbonate prepared in a catalyst system consisting of an alkali metal compound and a crown compound, Japanese Patent Laid-Open Publication No. S59-13776 used quaternary ammonium and alcohol, WO 2005/003113 used tetraalkyl phosphonium halide, and Korean Patent Laid-Open Publication No. 2005-0115694 used a catalyst system consisting of a metal salt and an aliphatic cyclic amine salt. However, these synthesis methods have problems in that since a reaction yield is low under mild reaction conditions, high temperature and a long period of reaction time are required to increase yield, and moisture contents of raw materials, i.e., carbon dioxide and alkylene oxide should be controlled to be hundreds of ppm or less.

U.S. Pat. No. 5,283,356 discloses a phthalocyanine catalyst including Co, Cr, Fe, Mn, Ni, Ti, V, Zr, etc., and Japanese Patent Laid-Open Publication No. H7-206547 discloses a catalyst substituted with rubidium (Rb) or cesium (Cs) ions instead of hydrogen ions of hetero polyacid, respectively. However, these catalysts are high cost, wherein a reaction temperature is high as 120° C. to 180° C., and a yield is low as 30 to 90%.

As described above, the catalyst used for industrial synthesis of the cyclic carbonate according to the related art has problems in that reaction conditions are complicated, for example, a reaction temperature should be high, a moisture content of raw materials should be significantly low, etc., and selectivity and yield are low, and a reaction time is long.

RELATED ART DOCUMENT

Patent Documents (Patent Document 1) Japanese Patent Laid-Open Publication No. S56-128778
(Patent Document 2) Japanese Patent Laid-Open Publication No. S59-13776
(Patent Document 3) WO 2005/003113
(Patent Document 4) Korean Patent Laid-Open Publication No. 2005-0115694
(Patent Document 5) U.S. Pat. No. 5,283,356.
(Patent Document 6) Japanese Patent Laid-Open Publication No. H7-206547

Non-Patent Documents (Non-Patent Document 1) Darensbourg, D. J.; Yarbrough, J. C. *J. Am. Chem. Soc.* 2002, 124, 6335-6342.
(Non-Patent Document 2) Qin, Z.; Thomas, C. M.; Lee, S.; Coates, G. W. *Angew. Chem. Int. Ed.* 2003, 42, 5484-5487.
(Non-Patent Document 3) North, M.; Pasquale, R. *Angew. Chem. Int. Ed.* 2009, 48, 2946-2948.
(Non-Patent Document 4) Whiteoak, C. J.; Kielland, N.; Laserna, V.; Escudero-Adán E. C.; Martin, E.; Kleij, A. W. *J. Am. Chem. Soc.* 2013, 135, 1228-1231.
(Non-Patent Document 5) Whiteoak, C. J.; Gjoka, B.; Martin, E.; Belmonte, M. M.; Escudero-Adán E. C.; Zonta, C.; Licini, G.; Kleij, A. W. *Inorg. Chem.* 2012, 51, 10639-10649.

SUMMARY

The present inventors found that selectivity for preparing cyclic carbonate through a reaction of alkylene oxide and carbon dioxide could be increased by a pre-organized rigid metal complex so as to have a cis-binding site available for reducing an activation barrier of the reaction, and completed the present disclosure.

An embodiment of the present invention is directed to providing a metal catalyst capable of selectively preparing cyclic carbonate by reacting alkylene oxide with carbon dioxide.

Another embodiment of the present invention is directed to providing a method for selectively preparing cyclic carbonate in a high yield by reacting alkylene oxide with carbon dioxide using the metal catalyst.

In addition, still another embodiment of the present invention is directed to providing the prepared cyclic carbonate, and an electrolyte including the same.

In one general aspect, a catalyst used for selectively preparing cyclic carbonate by reacting an alkylene oxide compound with carbon dioxide, and a method for preparing cyclic carbonate using the same.

Hereinafter, the present invention will be described in detail.

Here, unless technical and scientific terms used herein are defined otherwise, they have meanings generally understood by those skilled in the art to which the present invention pertains. In addition, repeated descriptions for technical constitution and function as the same as the related art will be omitted.

The present invention provides a catalyst for selectively preparing cyclic carbonate from alkylene oxide and carbon dioxide, and the catalyst of the present invention is a metal complex including a ligand represented by Chemical Formula 1 below and a trivalent metal in Group 8 or Group 13:

[Chemical Formula 1]

in Chemical Formula 1, $R^1$ is hydrogen, (C1-C20)alkyl or halogen; $R^2$ is hydrogen, (C1-C20)alkyl, (C1-C20)alkoxy, halogen or nitro.

The ligand represented by Chemical Formula 1 of the present invention has three phenolate donors bonded to a trisubstituted carbon and a salicylidene moiety.

The ligand represented by Chemical Formula 1 may be selected from the following structures, but is not limited thereto:

The ligand represented by Chemical Formula 1 is effectively prepared through an imidization reaction of dihydroxybenzophenone and ammonia, a reductive amination reaction, and a reaction with salicylaldehyde derivative.

More specifically, the ligand represented by Chemical Formula 1 is prepared by the following steps as shown in Reaction Scheme 1 below:

1) preparing an imine compound represented by Chemical Formula B by reacting dihydroxybenzophenone represented by Chemical Formula A with ammonia;

2) preparing a secondary amine compound represented by Chemical Formula C below by reducing the imine compound represented by Chemical Formula B; and 3) preparing the ligand represented by Chemical Formula 1 by reacting the secondary amine compound represented by Chemical Formula C with a salicylaldehyde derivative represented by Chemical Formula D:

[Reaction Scheme 1]

in Reaction Scheme 1, R¹ is hydrogen, (C1-C20)alkyl or halogen; R² is hydrogen, (C1-C20)alkyl, (C1-C20)alkoxy, halogen or nitro.

The imine compound represented by Chemical Formula B is prepared by reacting commercially available 2,2'-dihydroxybenzophenone represented by Chemical Formula A with ammonia. In general, it is significantly unstable to separate the imine compound formed from ammonia; however, the imine compound represented by Chemical Formula B may be separated due to internal hydrogen bonds present between an imine group and two phenol groups. The ammonia is used in an excessive amount relative to the 2,2'-dihydroxybenzophenone represented by Chemical Formula A, and is preferably used in an amount of 2 to 10 equivalents relative to 1 equivalent of the 2,2'-dihydroxybenzophenone represented by Chemical Formula A. The ammonia is preferably saturated aqueous ammonia. The imidization reaction is possible to be performed at a general reaction temperature, and preferably, may be performed at 20° C. to 40° C.

The preparation of the imine compound represented by Chemical Formula B may be performed under an organic solvent or by a neat reaction, wherein the organic solvent is not limited as long as it is capable of dissolving the reaction materials. The neat reaction is to perform the imidization reaction by mixing the dihydroxybenzophenone represented by Chemical Formula A with ammonia without using the organic solvent. A solvent for the reaction is preferably an inert solvent selected from the group consisting of methanol, ethanol, isopropanol, butanol, acetone, ethyl acetate, acetonitrile, isopropyl ether, methyl ethyl ketone, methylene chloride, dichlorobenzene, chlorobenzene, dichloroethane, tetrahydrofuran, toluene, benzene, xylene, mesitylene, dimethyl formamide, dimethyl sulfoxide, etc., in consideration of solubility of reaction materials and easiness of removal thereof, and more preferably, methanol, ethanol, or mixed solvents thereof.

The prepared imine compound represented by Chemical Formula B may be used for next reaction without further separation or purification, or may be subjected to purification if needed.

The prepared imine compound represented by Chemical Formula B is reduced by using a reducing agent to thereby prepare the secondary amine compound represented by Chemical Formula C. The reducing agent may be metal hydride, preferably, at least one selected from the group consisting of $NaBH_4$, $NaBH(OAc)_3$, $NaBH_2(OAc)_2$, $NaBH_3OAc$, $NaBH_3CN$, $KBH_4$, $KBH(OAc)$, $LiAlH_4$, $B_2H_6$ and DIBAL-H (diisobutylaluminium hydride), and more preferably, $NaBH_4$. The reducing agent is not limited in view of an amount, but is used in the same amount or an excess amount relative to the imine compound represented by Chemical Formula B. Preferably, the reducing agent is used at 1 to 5 equivalents relative to 1 equivalent of the imine compound represented by Chemical Formula B. The reduction reaction is possible to be performed at a general reaction temperature, and preferably, may be performed at 20° C. to 40° C.

The preparation of the secondary amine compound represented by Chemical Formula C may be performed under an organic solvent, wherein the organic solvent is not limited as long as it is capable of dissolving the reaction materials. A solvent for the reaction is preferably an inert solvent selected from the group consisting of methanol, ethanol, isopropanol, acetone, ethyl acetate, acetonitrile, isopropyl ether, methyl ethyl ketone, methylene chloride, dichlorobenzene, chlorobenzene, dichloroethane, tetrahydrofuran, toluene, benzene, and xylene in consideration of solubility of reaction materials and easiness of removal thereof, and more preferably, methanol, ethanol, or mixed solvents thereof.

The ligand represented by Chemical Formula 1 is prepared by reacting the secondary amine compound represented by Chemical Formula C with the salicylaldehyde derivative represented by Chemical Formula D. The salicylaldehyde derivative represented by Chemical Formula D is used in the same amount or an excess amount relative to the secondary amine compound represented by Chemical Formula C. Preferably, the salicylaldehyde derivative is used at 1 to 5 equivalent relative to 1 equivalent of the secondary amine compound represented by Chemical Formula C. In addition, in order to improve the reaction yield, the reaction may be performed by further including a base, wherein the base may be a tertiary organic amine. An example of the tertiary organic amine may be aliphatic amine represented by R'R''R'''N (wherein R', R'' and R''' are each independently (C1-C6)alkyl, (C2-C16)alkenyl, (C6-C12)aryl or benzyl). Specifically, examples of the tertiary organic amine may include trimethylamine, triethylamine, tripropylamine, dimethylethylamine, tributylamine, diisopropyl ethylamine, and triphenylamine, and preferably, trimethylamine or triethylamine. It is preferable that the reaction may be performed at 20° C. to 40° C.

The preparation of the ligand represented by Chemical Formula 1 may be performed under an organic solvent, wherein the organic solvent is not limited as long as it is capable of dissolving the reaction materials. A solvent for the reaction may be methanol, ethanol, isopropanol, acetone, ethyl acetate, acetonitrile, isopropyl ether, methyl ethyl ketone, methylene chloride, dichlorobenzene, chlorobenzene, dichloroethane, tetrahydrofuran, toluene, benzene, xylene, etc.

All reactions are completed after confirmation through TLC, etc., whether starting materials are completely consumed. When the reaction is completed, the solvent may be distilled under reduced pressure, and a target material may be separated and purified by general methods such as filtration, column chromatography, recrystallization, etc.

More specifically, the catalyst for selectively preparing the cyclic carbonate according to the present invention is represented by Chemical Formula 2 below:

[Chemical Formula 2]

in Chemical Formula 2, M is Fe or Al; $R^1$ is hydrogen, (C1-C20)alkyl or halogen; and $R^2$ is hydrogen, (C1-C20) alkyl, (C1-C20)alkoxy, halogen or nitro.

Figure 1:
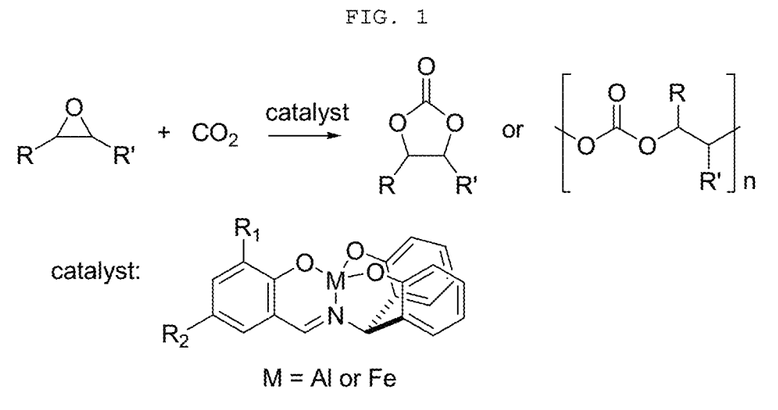
FIG. 1 illustrates Reaction Scheme for preparing cyclic carbonate using a catalyst according to the present invention.

The metal complex represented by Chemical Formula 2 according to the present invention includes a ligand consisting of a planar salicylidene group as well as a trisubstituted carbon center possessing a pre-organized bite angle ideal to accommodate a 6-coordinate metal center as illustrated in FIG. 1. Meanwhile, an amino tris(phenolate) ligand included in the catalyst for selectively preparing the cyclic carbonate according to the related art has three flexible methylene groups, and therefore, the enhanced rigidity effect of the ligand skeleton itself according to the present invention may not be observed in the related art.

More specifically, the metal complex represented by Chemical Formula 2 above according to an exemplary embodiment of the present invention may be selected from the following structures, but the present invention is not limited thereto:

The catalyst for selectively preparing the cyclic carbonate according to the present invention may be prepared by reacting the ligand compound represented by Chemical Formula 1 and a trivalent metal halide in Group 8 or Group 13.

In addition, the present invention provides a method for preparing cyclic carbonate by reacting carbon dioxide with alkylene oxide using the metal complex represented by Chemical Formula 2 as a catalyst, wherein the alkylene oxide which is a reaction material includes at least one epoxide in the chemical structure, and in the reaction with carbon dioxide, all epoxides react with carbon dioxide to form the cyclic carbonate.

More specifically, the present invention provides a method for preparing cyclic carbonate represented by Chemical Formula 4 below by reacting carbon dioxide with alkylene oxide represented by Chemical Formula 3 below, using the metal complex represented by Chemical Formula 2 above as a catalyst:

[Chemical Formula 2]

[Chemical Formula 3]

[Chemical Formula 4]

in Chemical Formulas 2, 3 and 4,

M is Fe or Al;

$R^1$ is hydrogen, (C1-C20)alkyl or halogen;

$R^2$ is hydrogen, (C1-C20)alkyl, (C1-C20)alkoxy, halogen or nitro;

$R^{1a}$ and $R^{4a}$ are each independently hydrogen, (C1-C10)alkyl, halo(C1-C10)alkyl or (C6-C12)aryl, and $R^{1a}$ and $R^{4a}$ may be linked via (C3-C5)alkylene with or without a fused ring to form a ring, wherein the formed ring may be further substituted with vinyl, $-(CH_2)_aSiR^{11}R^{12}R^{13}$, oxiranyl or (7-oxa-bicyclo[4.1.0]heptane-3-yl)acetyl;

$R^{3b}$ and $R^{4b}$ are each independently hydrogen, (C1-C10)alkyl, halo(C1-C10)alkyl or (C6-C12)aryl, and $R^{3b}$ and $R^{4b}$ may be linked via (C3-C5)alkylene with or without a fused ring to form a ring, wherein $CH_2$ of the alkylene may be substituted with O, and the formed ring may be further substituted with vinyl, $-(CH_2)_aSiR^{11}R^{12}R^{13}$, 1,3-dioxolan-2-one-4-yl or (hexahydrobenzo[d][1,3]dioxol-2-one-5-yl)acetyl;

$R^{11}$ to $R^{13}$ are each independently (C1-C10)alkyl or (C1-C10)alkoxy; and a is an integer of 1 to 5.

The term "alkyl" used herein means monovalent linear or branched saturated hydrocarbon radical only consisting of carbon atoms and hydrogen atoms, and examples of the alkyl radical include methyl, ethyl, propyl, isopropyl, butyl, isobutyl, t-butyl, pentyl, hexyl, octyl, dodecyl, etc., but the present invention is not limited thereto.

The term "haloalkyl" used herein means alkylradical substituted with halogen atom as defined above, and examples of the haloalkyl include fluoromethyl, difluoromethyl, trifluoromethyl, fluoroethyl, difluoroethyl, bromopropyl, etc., but the present invention is not limited thereto.

The term "aryl" used herein is an organic radical derived from aromatic hydrocarbon due to removal of one hydrogen, and includes a single ring system or a fused ring system including 4 to 7 ring atoms, preferably, 5 or 6 ring atoms in each ring, and even includes a form in which a plurality of aryls are connected by a single bond. Specific examples of aryl include phenyl, naphthyl, biphenyl, anthryl, indenyl, fluorenyl, etc., but the present invention is not limited thereto.

The term "alkoxy" used herein means —O-alkyl radical, wherein the 'alkyl' is the same as described above. Examples of the alkoxy radical include methoxy, ethoxy, isopropoxy, butoxy, isobutoxy, t-butoxy, etc., but the present invention is not limited thereto.

In the method for preparing cyclic carbonate according to an exemplary embodiment of the present invention, the alkylene oxide represented by Chemical Formula 3 is more preferably an epoxide derivative fused with 5-membered to 7-membered ring, and specifically, may be selected from the following structures, but the present invention is not limited thereto:

$R^{11}$ is hydrogen, vinyl, $-(CH_2)_aSiR^{11}R^{12}R^{13}$, oxiranyl or ((7-oxa-bicyclo[4.1.0]heptane-3-yl)acetyl).

In the method for preparing cyclic carbonate according to an exemplary embodiment of the present invention, the metal complex represented by Chemical Formula 2 is preferably used in an amount of 0.1 to 2.0 mol % relative to the alkylene oxide represented by Chemical Formula 3, wherein when the used amount of the metal complex is less than 0.1 mol %, a reaction speed is excessively decreased, and when the used amount thereof is more than 2.0 mol %, the reaction speed and the selectivity are not improved any more, such that economical efficiency in using the catalyst is deteriorated.

In the method for preparing cyclic carbonate according to an exemplary embodiment of the present invention, an ammonium co-catalyst or an amine-based co-catalyst may be further included for an improved reaction speed and high yield, wherein the ammonium co-catalyst or the amine-based co-catalyst is preferably used in an amount of 0.1 to 10.0 mol % relative to the alkylene oxide represented by Chemical Formula 3. The ammonium co-catalyst may be aliphatic amine salts, aromatic amine salts, or heteroaromatic amine salts, and specifically, may be selected from the group consisting of tetrabutylammonium bromide ($NBu_4Br$), tetramethylammonium bromide ($NMe_4Br$), tetraethylammonium tetrafluoroborate ($NEt_4BF_4$), tetrapropylammonium bromide ($NPr_4Br$), tetrahexylammonium chloride ($N[(CH_2)_5CH_3]_4Cl$), tetrapentylammonium bromide ($N[(CH_2)_4CH_3]_4Br$), tetraheptylammonium bromide ($N[(CH_2)_6CH_3]_4Br$), tetraoctylammonium bromide ($N[CH_2)_7CH_3]_4Br$), trimethyldodecylammonium chloride ($CH_3(CH_2)_{11}N(CH_3)_3Cl$), trimethyltetradecylammonium bromide ($CH_3(CH_2)_{13}N(CH_3)_3Br$), trimethylhexadecylammonium chloride ($CH_3(CH_2)_{15}N(CH_3)_3Cl$), methyltrioctylammonium chloride ($CH_3N[(CH_2)_7CH_3]_3Cl$), tetrabutylammonium fluoride ($NBu_4F$), tetrabutylammonium chloride ($NBu_4Cl$), tetrabutylammonium iodide ($NBu_4I$), 1-butyl-3-methylimidazolium bromide ([bmim]Br), 1-butyl-3-methylimidazolium chloride ([bmim]Cl), and bis(triphenylphosphine)iminium chloride ($[((C_6H_5)_3P)_2N]Cl$, PPNCl), and the amine-based co-catalyst may be specifically selected from the group consisting of triethylamine ($Et_3N$), 1,8-diazabicycloundec-7-ene (DBU), pyridine ($C_5H_5N$), and 4-dimethylaminopyridine ($C_7H_{10}N_2$, DMAP), and the co-catalyst is preferably tetrabutylammonium bromide ($NBu_4Br$).

Even though carbon dioxide and the alkylene oxide contain nitrogen, hydrogen, carbon monoxide, a low concentration of hydrocarbon, or water, they do not significantly affect on the reaction. Industrially produced carbon dioxide and alkylene oxide are usable without further purification.

In the method for preparing cyclic carbonate according to an exemplary embodiment of the present invention, the reaction temperature is preferably 25☐ to 120☐. When the reaction temperature is excessively low, the reaction speed is decreased. When the reaction temperature is excessively high, alkylene oxide which is the raw material degraded, or self-polymerization occurs, which deteriorates selectivity of the cyclic carbonate. In addition, in the reaction, carbon dioxide is supplied in a reactor under a pressure of 1 bar to 10 bar. When a reaction pressure is less than 1 bar, the reaction speed is remarkably decreased, and when the reaction pressure is more than 10 bar, there is no improvement effect with the reaction speed, which is not economical.

In the method for preparing cyclic carbonate according to an exemplary embodiment of the present invention, the reaction may be performed under an organic solvent or by a neat reaction. The neat reaction is to react carbon dioxide with alkylene carbonate without using the organic solvent. In some cases, an organic solvent is usable to prevent rapid heat generation. The organic solvent to be usable may be any solvent that is generally used in the art. For example, the organic solvent may be methylene chloride, chloroform, ethyl acetate, tert-methylbutylether, toluene, isopropylalcohol, dioxane, acetonitrile, alkylene carbonate, etc., but the present invention is not limited thereto.

Further, the present invention relates to the prepared cyclic carbonate and an electrolyte including the same, wherein the cyclic carbonate is represented by Chemical Formula 4 below:

[Chemical Formula 4]

in Chemical Formula 4, $R^{3b}$ and $R^{4b}$ are each independently hydrogen, (C1-C10)alkyl, halo(C1-C10)alkyl or (C6-C12)aryl, and $R^{3b}$ and $R^{4b}$ may be linked via (C3-C5) alkylene with or without a fused ring to form a ring, wherein the formed ring may be further substituted with vinyl, —(CH$_2$)$_a$SiR$^{11}$R$^{12}$R$^{13}$, 1,3-dioxolan-2-one-4-yl or (hexahydrobenzo[d][1,3]dioxol-2-one-5-yl)acetyl;

$R^{11}$ to $R^{13}$ are each independently (C1-C10)alkyl or (C1-C10)alkoxy; and a is an integer of 1 to 5.

The cyclic carbonate represented by Chemical Formula 4 according to an exemplary embodiment of the present invention may be represented by Chemical Formula 5 or 6 below:

[Chemical Formula 5]

[Chemical Formula 6]

in Chemical Formulas 5 and 6, $L^1$ and $L^2$ are each independently O or (C1-C3)alkylene, and the alkylene may be further substituted with vinyl, —(CH$_2$)$_a$SiR$^{11}$R$^{12}$R$^{13}$, 1,3-dioxolan-2-one-4-yl or (hexahydrobenzo[d][1,3]dioxol-2-one-5-yl)acetyl;

$R^{11}$ to $R^{13}$ are each independently (C1-C10)alkyl or (C1-C10)alkoxy; and a is an integer of 1 to 5.

The cyclic carbonate according to an exemplary embodiment of the present invention may be selected from the following structures, but the present invention is not limited thereto:

The cyclic carbonate represented by Chemical Formula 4 above according to the present invention may be used as a solvent or an additive constituting an electrolyte in a lithium secondary battery to exhibit more stable and excellent electrolyte performance.

DETAILED DESCRIPTION OF EMBODIMENTS

Hereinafter, a configuration of the present invention will be described in detail with reference to Examples. These Examples are provided only for assisting in the entire understanding of the present invention, and it will be obvious to those skilled in the art that the scope of the present invention is not construed to be limited to these examples.

Commercially available reagents and carbon dioxide (99.99%) were used without further purification or drying. All reactions were performed in a 80 mL stainless steel reactor. $^1$H NMR (400 MHz) and $^{13}$C NMR (100 MHz) analyses were recorded on a Bruker Advance III HD spectrometer. The mass spectra were analyzed on a High Resolution Hybrid Tandem LC-MS/MS spectrometer.

[Preparation Examples 1 to 8] Preparation of Ligands 1a to 1h 1a (R$_1$ = H, R$_2$ = H)
1b (R$_1$ = H, R$_2$ = NO$_2$)
1c (R$_1$ = Cl, R$_2$ = Cl)
1d (R$_1$ = H, R$_2$ = F)
1e (R$_1$ = H, R$_2$ = OMe)
1f (R$_1$ = H, R$_2$ = Me)
1g (R$_1$ = t-Bu, R$_2$ = t-Bu)
1h (R$_1$ = t-Bu, R$_2$ = NO$_2$)

Preparation of Compound B

To a stirred solution of 2,2'-dihydroxybenzophenone (Compound A, DHBP) (30 g, 140 mmol) in MeOH (300 mL), 4 equivalents of saturated ammonia (38 mL, 560 mmol) was added at ambient temperature, followed by stirring for 16 hours. As the reaction proceeded, since it was difficult to stir, methanol (300 mL) was additionally added during the stirring. The formation of Compound B was confirmed by $^1$H NMR (in DMSO-d$_6$). When the reaction was completed, yellow precipitate was filtered and washed with methanol to obtain Compound B as a yellow solid (26.7 g, 90% yield).

$^1$H NMR (400 MHz, DMSO-d$_6$): δ 7.33-7.29 (m, 2H), 7.06-7.05 (d, 2H), 6.90-6.88 (d, 2H), 6.76-6.72 (br, 2H); $^{13}$C NMR (100 MHz, DMSO-d$_6$): δ 177.3, 132.4, 130.0, 117.8, 117.1; HRMS (ESI) m/z calculated for C$_{13}$H$_{12}$NO$_2$ [H$^+$]: 214.0868, found: 214.0867.

Preparation of Compound C

To a stirred mixture of the Compound B (20 g, 94 mmol) in methanol (200 mL), NaBH$_4$ (6.4 g, 170 mmol, 1.8 equiv.) was added at ambient temperature, followed by stirring for 1 hour. Then, saturated HCl aqueous solution (24.3 ml, 28 mmol, 3 equiv.) was slowly added at 0° C., followed by stirring for 30 minutes. Solvent was evaporated thoroughly and the product was redissolved in ethanol. White solid (Na salt) was precipitated and removed with filtration. The ethanol solution was concentrated and CHCl$_3$ was added to obtain a white solid. The white solid product was filtered to obtain Compound C (21.6 g, 91% yield).

$^1$H NMR (400 MHz, DMSO-d$_6$): δ 10.32 (s, 2H), 8.65 (s, 3H), 7.32-7.29 (dd, 2H), 7.19-7.15 (m, 2H), 7.07-7.05 (dd, 2H), 6.83-6.79 (t, 2H), 5.87-5.86 (d, 1H); $^{13}$C NMR (100 MHz, DMSO-d$_6$): δ 155.0, 129.4, 128.4, 123.4, 118.8, 115.7, 47.4; HRMS (ESI) m/z calculated for C$_{13}$H$_{14}$NO$_2$ [H$^+$]: 216.1019, found: 216.1002.

Preparation of Compound 1a

To a methanol solution of the Compound C (4 g, 15.9 mmol), triethylamine (2.3 ml, 16.7 mmol, 1.05 equiv.) and salicylaldehyde (16.7 mmol, 1.05 equiv.) were added and stirred. The degree of reaction was monitored using $^1$H NMR, and after 1 hour of the stirring, a prepared yellow solid was filtered and washed with methanol to obtain a compound 1a (84% yield).

Preparation Example 1: Compound 1a $^1$H NMR (400 MHz, DMSO-$d_6$): δ 13.90 (s, 1H), 9.56 (s, 2H), 8.65 (s, 1H), 7.47-7.44 (dd, 1H), 7.34-7.30 (m, 1H), 7.14-7.08 (m, 4H), 6.89-6.84 (m, 4H), 6.82-6.78 (td, 2H); $^{13}$C NMR (100 MHz, DMSO-$d_6$): δ 164.8, 160.8, 154.8, 132.4, 131.8, 128.2, 128.1, 127.8, 118.8, 118.8, 118.5, 116.5, 115.3, 63.7; HRMS (ESI) m/z calculated for $C_{20}H_{18}NO_3$ [H]$^+$: 320.1287, found: 320.1271.

Preparation of Compound 1b

Compound 1b (yellow solid, 87% yield) was obtained by performing the same method as the preparation method of Compound 1a except for using 5-nitrosalicylaldehyde (16.7 mmol, 1.05 equiv.) instead of using salicylaldehyde.

Preparation Example 2: Compound 1b $^1$H NMR (400 MHz, DMSO-$d_6$): δ 15.15 (s, 1H), 10.02 (s, 2H), 8.94 (s, 1H), 8.51-8.50 (d, 1H), 8.07-8.04 (dd, 1H), 7.20-7.10 (td, 2H), 7.13-7.10 (dd, 2H), 6.89-6.87 (dd, 2H), 6.84-6.80 (td, 2H), 6.65-6.53 (d, 1H), 6.33 (s, 1H); $^{13}$C NMR (100 MHz, DMSO-$d_6$): δ 176.6, 165.9, 155.0, 134.5, 132.2, 129.2, 128.5, 124.5, 122.2, 119.1, 115.6, 114.0, 62.0; HRMS (ESI) m/z calculated for $C_{20}H_{17}N_2O_5$ [H]$^+$: 365.1137, found: 365.1109.

Preparation of Compound 1c

To a methanol solution of the Compound C (4 g, 15.9 mmol), triethylamine (2.3 ml, 16.7 mmol, 1.05 equiv.) and 3,5-dichlorosalicylaldehyde (16.7 mmol, 1.05 equiv.) were added and stirred. The degree of reaction was monitored using $^1$H NMR, and after 1 hour of the stirring, solvent was concentrated by evaporation, followed by recrystallization using chloroform to obtain Compound 1c (Yellow solid, 66% yield).

Preparation Example 3: Compound 1c $^1$H NMR (400 MHz, DMSO-$d_6$): δ 15.34 (s, 1H), 9.87 (s, 2H), 7.58-7.57 (d, 1H), 7.51-7.50 (d, 1H), 7.17-7.11 (m, 4H), 6.87-6.85 (dd, 2H), 7.13-7.10 (dd, 2H), 6.83-6.79 (td, 2H), 6.31 (s, 1H); $^{13}$C NMR (100 MHz, DMSO-$d_6$): δ 164.4, 162.9, 154.9, 132.8, 130.5, 128.8, 128.4, 125.6, 124.3, 119.0, 117.5, 117.1, 115.5, 62.1; HRMS (ESI) m/z calculated for $C_{20}H_{16}N_1O_3Cl_2$ [H]$^+$: 388.0507, found: 388.0461.

Preparation of Compound 1d

Compound 1d (yellow solid, 59% yield) was obtained by performing the same method as the preparation method of Compound 1a except for using 5-fluorosalicylaldehyde (16.7 mmol, 1.05 equiv.) instead of using salicylaldehyde.

Preparation Example 4: Compound 1d $^1$H NMR (400 MHz, DMSO-$d_6$): δ 13.58 (s, 1H), 9.57 (s, 2H), 8.63 (s, 1H), 7.42-7.38 (dd, 1H), 7.22-7.15 (td, 1H), 7.12-7.07 (m, 4H), 6.90-6.76 (m, 5H), 6.28 (s, 1H).

Preparation of Compound 1e

To a methanol solution of the Compound C (350 mg, 1.39 mmol, 1.0 equiv.), triethylamine (0.19 mL, 1.39 mmol, 1.0 equiv.) and 5-methoxysalicylaldehyde (1.39 mmol, 1.0 equiv) were added and stirred. The degree of reaction was monitored using $^1$H NMR, and after 6 hours of the stirring, solvent was evaporated, and the obtained mixture was dissolved in ethyl acetate, and washed with water. The ethyl acetate solution was dried over magnesium sulfide, and solvent was evaporated, followed by recrystallization using chloroform and hexane to obtain Compound 1e (yellow solid, 88% yield).

Preparation Example 5: Compound 1e $^1$H NMR (400 MHz, DMSO-$d_6$): δ 13.19 (s, 1H), 9.51 (s, 2H), 8.59 (s, 1H), 7.11-7.07 (m, 5H), 6.96-6.92 (dd, 1H), 6.82-6.75 (m, 5H), 6.28 (s, 1H), 3.70 (s, 3H).

Preparation of Compound 1f

Compound 1f (yellow solid, 73% yield) was obtained by performing the same method as the preparation method of Compound 1c except for using 5-methylsalicylaldehyde (16.7 mmol, 1.05 equiv.) instead of using 3,5-dichlorosalicylaldehyde.

Preparation Example 6: Compound 1f $^1$H NMR (400 MHz, DMSO-$d_6$): δ 13.50 (s, 1H), 9.56 (s, 2H), 8.55 (s, 1H), 7.24 (s, 1H), 7.15-7.06 (m, 5H), 6.84-6.75 (m, 5H), 6.27 (s, 1H), 2.22 (s, 3H).

Preparation of Compound 1g

To a methanol solution of the Compound C (350 mg, 1.39 mmol, 1.0 equiv.), triethylamine (0.19 mL, 1.39 mmol, 1.0 equiv.) and 3,5-di-t-butylsalicylaldehyde (1.39 mmol, 1.0 equiv) were added and stirred. The degree of reaction was monitored using $^1$H NMR, and after 6 hours of the stirring, solvent was evaporated, and the obtained mixture was dissolved in ethyl acetate, and washed with water. The ethyl acetate was dried over magnesium sulfide, and evaporated to obtain Compound 1g (yellow solid, 89% yield).

Preparation Example 7: Compound 1g $^1$H NMR (400 MHz, DMSO-$d_6$): δ 14.45 (s, 1H), 9.44 (s, 2H), 8.65 (s, 1H), 7.32-7.28 (dd, 2H), 7.15-7.08 (m, 4H), 6.87-6.85 (dd, 2H), 6.82-6.78 (td, 2H), 6.36 (s, 1H), 1.39 (s, 9H), 1.32 (s, 9H); $^{13}$C NMR (100 MHz, DMSO-$d_6$): δ 166.1, 157.8, 154.8, 139.6, 135.6, 128.2, 128.0, 128.0, 126.5, 126.1, 118.8, 117.9, 115.3, 63.4, 34.6, 33.8, 31.3, 29.3; HRMS (ESI) m/z calculated for $C_{28}H_{34}N_1O_3$ [H$^+$]: 432.2539, found: 432.2553.

Preparation of Compound 1h

Compound 1h (yellow solid, 73% yield) was obtained by performing the same method as the preparation method of Compound 1e except for using 3-t-butyl-5-nitrosalicylaldehyde (1.39 mmol, 1.0 equiv) instead of using 5-methoxysalicylaldehyde.

Preparation Example 8: Compound 1h $^1$H NMR (400 MHz, DMSO-$d_6$): δ 15.14 (s, 1H), 10.07 (s, 2H), 8.92-8.89 (d, 1H), 8.40-8.39 (d, 1H), 7.94-7.93 (d, 1H), 7.21-7.17 (td, 2H), 7.13-7.11 (dd, 2H), 6.91-6.89 (dd, 2H), 6.86-6.82 (td, 2H), 6.32-6.31 (d, 1H), 1.34 (s, 9H); $^{13}$C NMR (100 MHz, DMSO-$d_6$): δ 177.7, 166.6, 155.0, 141.9, 133.2, 131.3, 129.4, 128.6, 124.5, 124.2, 119.1, 115.6, 113.5, 61.8, 34.8, 28.7; HRMS (ESI) m/z calculated for $C_{24}H_{25}N_2O_5$ [H$^+$]: 421.1763, found: 421.1758.

[Examples 1 to 10] Preparation of Metal Complex 1a (R$_1$ = H, R$_2$ = H)
1b (R$_1$ = H, R$_2$ = NO$_2$)
1c (R$_1$ = Cl, R$_2$ = Cl)
1d (R$_1$ = H, R$_2$ = F)
1e (R$_1$ = H, R$_2$ = OMe)
1f (R$_1$ = H, R$_2$ = Me)
1g (R$_1$ = t-Bu, R$_2$ = t-Bu)
1h (R$_1$ = t-Bu, R$_2$ = NO$_2$)

Fe-1a (M = Fe, R$_1$ = H, R$_2$ = H)
Fe-1b (M = Fe, R$_1$ = H, R$_2$ = NO$_2$)
Fe-1c (M = Fe, R$_1$ = Cl, R$_2$ = Cl)
Fe-1d (M = Fe, R$_1$ = H, R$_2$ = F)
Fe-1e (M = Fe, R$_1$ = H, R$_2$ = OMe)
Fe-1f (M = Fe, R$_1$ = H, R$_2$ = Me)
Fe-1g (M = Fe, R$_1$ = t-Bu, R$_2$ = t-Bu)
Fe-1h (M = Fe, R$_1$ = t-Bu, R$_2$ = NO$_2$)
Al-1a (M = Al, R$_1$ = H, R$_2$ = H)
Al-1b (M = Al, R$_1$ = H, R$_2$ = NO$_2$)

[Example 1] Preparation of Metal Complex Fe-1a

To a methanol mixture of the Compound 1a (300 mg, 0.94 mmol), FeCl$_3$ (152 mg, 0.94 mmol, 1 equiv.) and triethylamine (285 mg, 2.82 mmol, 3 equiv.) were added and stirred for 12 hours. After the stirring was completed, a prepared brown solid was filtered and washed with methanol to obtain a metal complex Fe-1a (72% yield).

Figure 2:
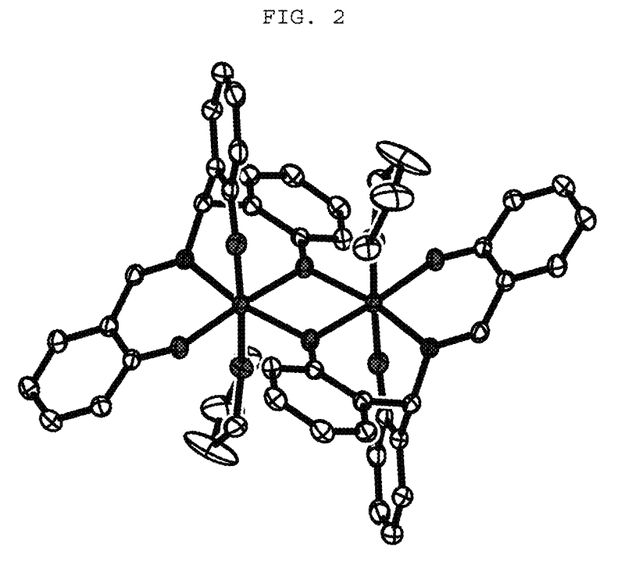
FIG. 2 illustrates a crystalline structure of a metal complex [Fe-1a.THF]$_2$ of Example 1.

UV-Vis [THF, nm (L mol$^{-1}$ cm$^{-1}$)]: ~260 (sh, 40000), ~342 (sh, 10000), 423 (7000). IR (KBr pellet, cm$^{-1}$): 3465, 3064, 3045, 2996, 2894, 1627, 1616, 1546, 1481, 1479, 1401, 1295, 1151, 1114, 1037, 887, 823, 755; HRMS (ESI) m/z calculated for [{C$_{20}$H$_{14}$FeN$_1$O$_3$}$_2$+Na]$^+$: 767.05, found: 766.87; Anal. calculated for C$_{40}$H$_{28}$Fe$_2$N$_2$O$_6$·2EtOH: C, 63.18; H, 4.82; N, 3.35. Found: C, 63.18; H, 5.05; N, 3.21. Crystal required for structural analysis through X-ray diffraction was obtained by slowly diffusing diethyl ether in saturated tetrahydrofuran (THF) solution of Fe-1a (FIG. 2).

[Example 2] Preparation of Metal Complex Fe-1b

A metal complex Fe-1b (85% yield) was obtained by performing the same method as the preparation of the metal complex Fe-1a except for using the Compound 1b instead of using the Compound 1a.

Figure 3:
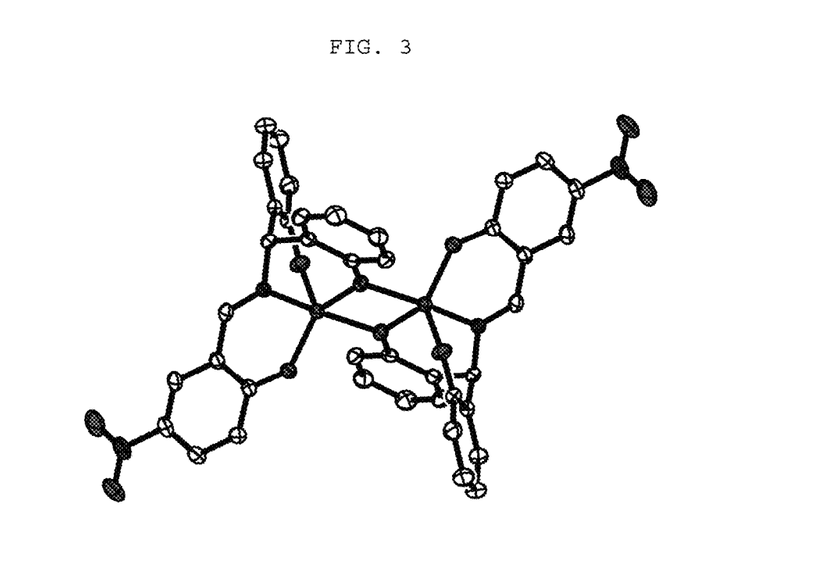
FIG. 3 illustrates a crystalline structure of a metal complex [Fe-1b]$_2$ of Example 2.

UV-Vis [THF, nm (L mol$^{-1}$ cm$^{-1}$)]: 276 (30000), 346 (30000), ~460 (sh, 6000). IR (KBr pellet, cm$^{-1}$): 3471, 3075, 3006, 2902, 2637, 1610, 1587, 1482, 1473, 1394, 1319, 1101, 1035, 954, 894, 846, 755; HRMS (ESI) m/z calculated for [{C$_{20}$H$_{13}$FeN$_2$O$_5$}$_2$+Na]$^+$: 857.02, found: 856.80; Anal. Calculated for C$_{40}$H$_{26}$Fe$_2$N$_4$O$_{10}$·2EtOH: C, 57.04; H, 4.13; N, 6.05. Found: C, 57.21; H, 4.27; N, 5.81. Crystal required for structural analysis through X-ray diffraction was obtained by slowly evaporating saturated benzene (THF) solution of Fe-1b (FIG. 3).

[Example 3] Preparation of Metal Complex Fe-1c

A metal complex Fe-1c (85% yield) was obtained by performing the same method as the preparation of the metal complex Fe-1a except for using the Compound 1c instead of using the Compound 1a.

IR (KBr pellet, cm$^{-1}$): 3641, 3429, 3057, 3010, 2970, 2925, 2891, 1626, 1560, 1528, 1483, 1477, 1441, 1416, 1388, 1302, 1290, 1267, 1242, 1223, 1180, 1117, 1105, 1066, 1034, 970, 937, 889, 863, 802, 794, 775, 755.

[Example 4] Preparation of Metal Complex Fe-1d

A metal complex Fe-1d (98% yield) was obtained by performing the same method as the preparation of the metal complex Fe-1a except for using the Compound 1d instead of using the Compound 1a.

IR (KBr pellet, cm$^{-1}$): 3627, 3419, 3057, 3012, 2891, 1691, 1626, 1595, 1552, 1477, 1466, 1450, 1387, 1290, 1267, 1254, 1225, 1188, 1147, 1117, 1066, 1034, 985, 968, 937, 895, 860, 822, 756.

[Example 5] Preparation of Metal Complex Fe-1e

A metal complex Fe-1e (77% yield) was obtained by performing the same method as the preparation of the metal complex Fe-1a except for using the Compound 1e instead of using the Compound 1a.

IR (KBr pellet, cm$^{-1}$): 3430, 3055, 3006, 2935, 2900, 2835, 1626, 1610, 1547, 1477, 1450, 1388, 1348, 1290, 1267, 1196, 1161, 1112, 1071, 1031, 895, 823, 756.

[Example 6] Preparation of Metal Complex Fe-1f

A metal complex Fe-1f (94% yield) was obtained by performing the same method as the preparation of the metal complex Fe-1a except for using the Compound 1f instead of using the Compound 1a.

IR (KBr pellet, cm$^{-1}$): 3415, 3055, 3012, 2920, 2866, 1624, 1595, 1545, 1477, 1450, 1385, 1292, 1267, 1238, 1227, 1165, 1138, 1115, 1070, 1036, 893, 856, 825, 814, 754.

[Example 7] Preparation of Metal Complex Fe-1g

A metal complex Fe-1g (93% yield) was obtained by performing the same method as the preparation of the metal complex Fe-1a except for using the Compound 1g instead of using the Compound 1a.

IR (KBr pellet, cm$^{-1}$): 3060, 3002, 2958, 2904, 2870, 1622, 1597, 1558, 1539, 1477, 1450, 1412, 1388, 1361, 1301, 1255, 1219, 1173, 1116, 1070, 1036, 1011, 930, 916, 887, 847, 820, 800, 791, 752.

[Example 8] Preparation of Metal Complex Fe-1h

A metal complex Fe-1h (82% yield) was obtained by performing the same method as the preparation of the metal complex Fe-1a except for using the Compound 1h instead of using the Compound 1a.

IR (KBr pellet, cm$^{-1}$): 3417, 3062, 3006, 2958, 2908, 2870, 1633, 1595, 1566, 1502, 1481, 1450, 1442, 1419, 1392, 1311, 1288, 1267, 1244, 1200, 1180, 1153, 1117, 1068, 1036, 985, 926, 889, 845, 820, 800, 754.

[Example 9] Preparation of Metal Complex Al-1a

To a tetrahydrofuran solution of Compound 1a (300 mg, 0.94 mmol), 2.0 M AlMe$_3$ heptane solution (0.47 ml, 0.94 mmol, 1 equiv.) was added and stirred for 3 hours. After the stirring was completed, solvent was evaporated to be concentrated, and hexane was added to obtain a white solid. The white solid was filtered to obtain Al-1a (62% yield).

Figure 4:
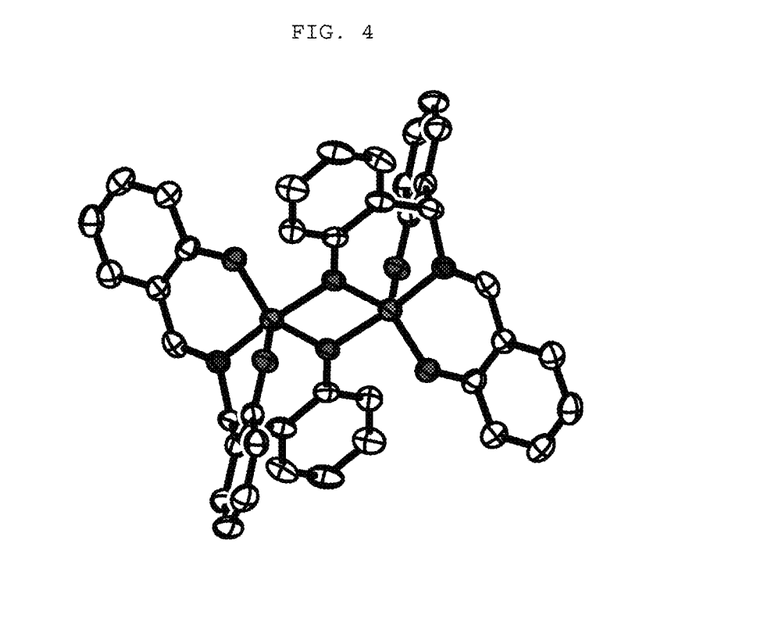
FIG. 4 illustrates a crystalline structure of a metal complex [Al-1a]$_2$ of Example 9.

$^1$H NMR (400 MHz, DMSO-d$_6$): δ 8.67 (s, 1H), 7.38 (m, 2H), 7.22 (d, 2H), 6.96 (t, 2H), 6.83 (d, 1H), 6.78 (t, 1H), 6.58 (m, 4H), 5.67 (s, 1H); $^{13}$C NMR (100 MHz, DMSO-d$_6$): δ 164.5, 163.4, 158.4, 134.8, 133.3, 130.1, 128.3, 127.7, 120.9, 120.1, 119.7, 117.1, 116.4, 76.3; UV-Vis [THF, nm (L mol$^{-1}$ cm$^{-1}$)]: 265 (33000), 273 (30000), 294 (13000), 337 (10000); IR (KBr pellet, cm$^{-1}$): 3056, 3029, 3008, 2969, 2923, 2886, 1633, 1606, 1554, 1482, 1457, 1405, 1311, 1294, 1274, 1240, 1214, 1186, 1151, 1132, 1116, 1076, 1035, 906, 894, 860, 835, 817, 794, 755; HRMS (ESI) m/z calculated for [{C$_{40}$H$_{28}$N$_2$O$_6$}+Na]$^+$: 709.15, found: 709.15. Anal. Calculated for C$_{40}$H$_{28}$Al$_2$N$_2$O$_6$: C, 69.97; H, 4.11; N, 4.08. Found: C, 69.42; H, 4.26; N, 3.94. Crystal required for structural analysis through X-ray diffraction was obtained by slowly diffusing diethyl ether in saturated tetrahydrofuran (THF) solution of Al-1a (FIG. 4).

[Example 10] Preparation of Metal Complex Al-1b

A metal complex Al-1b (70% yield) was obtained by performing the same method as the preparation of the metal complex Al-1a except for using the Compound 1b instead of using the Compound 1a.

Figure 5:
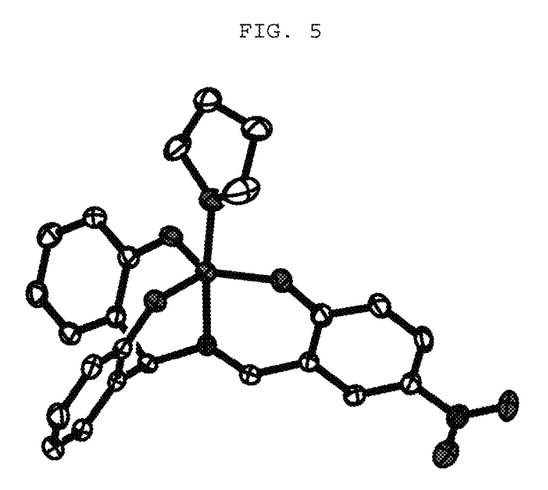
FIG. 5 illustrates a crystalline structure of a metal complex Al-1b.THF of Example 10.

$^1$H NMR (400 MHz, DMSO-d$_6$): δ 8.66 (s, 1H), 8.39 (s, 1H), 8.09 (dd, 1H), 7.07 (dd, 2H), 6.89 (td, 2H), 6.69 (d, 1H), 6.46 (dd, 2H), 6.41 (td, 2H), 5.46 (s, 1H); $^{13}$C NMR (100 MHz, DMSO-d$_6$): δ 171.6, 162.5, 160.2, 135.3, 130.4, 130.1, 128.8, 128.0, 127.4, 121.7, 119.6, 119.5, 114.4, 77.9, 67.0, 25.1; UV-Vis [THF, nm (L mol$^{-1}$ cm$^{-1}$)]: ~249 (sh, 22000), 262 (19000), ~278 (sh, 15000), 294 (13000), 325 (16000). IR (KBr pellet, cm$^{-1}$): 3060, 2989, 2981, 2910, 1650, 1602, 1565, 1488, 1394, 1336, 1303, 1209, 1130, 1101, 1045, 1035, 1014, 954, 904, 833, 800, 754, 692, 626; HRMS (ESI) m/z calculated for C$_{20}$H$_{14}$AlN$_2$O$_5$ [H]$^+$: 389.07, found: 389.07; Anal. Calculated for C$_{20}$H$_{13}$AlN$_2$O$_5$: C, 62.61; H, 4.60; N, 6.08. Found: C, 62.62; H, 4.69; N, 5.92. Crystal required for structural analysis through X-ray diffraction was obtained by slowly diffusing pentane in saturated tetrahydrofuran (THF) solution of Al-1a (FIG. 5).

[Example 11] Preparation of Cyclic Carbonate Using Carbon Dioxide and Cyclohexene Oxide To a 80 mL stainless steel reactor, 0.5 mol % catalyst, 2.5 mol % tetrabutylammonium bromide (NBu$_4$Br), and 1 ml of cyclohexene oxide were charged. The reactor was charged and discharged with 5 bar of CO$_2$ twice and finally charged with 10 bar of CO$_2$. The reactor was sealed, followed by stirring at 100° C. to perform the reaction. After the reaction was completed, an aliquot of the reaction mixture was dissolved in CDCl$_3$ and analyzed by $^1$H NMR.

Each catalyst, reaction time, and yield and selectivity of the products were shown in Table 1 below.

TABLE 1

| Entry | Catalyst | Reaction Time (h) | Yield (%) | Selectivity (I:II) |
|---|---|---|---|---|
| 1 | Fe-1a | 2 | 45 | >50:1 |
| 2 | Fe-1a | 8 | 83 | 23:1 |
| 3 | Fe-1b | 8 | 80 | 49:1 |
| 4 | Fe-1c | 8 | 89 | 20:1 |
| 5 | Fe-1d | 8 | 91 | 9:1 |
| 6 | Fe-1e | 8 | 75 | 8:1 |
| 7 | Fe-1f | 8 | 71 | 23:1 |
| 8 | Fe-1g | 8 | 87 | 2:1 |
| 9 | Fe-1h | 8 | 84 | 5:1 |
| 10 | Al-1a | 8 | 92 | 1.1:1 |
| 11 | Al-1b | 8 | 89 | 1.8:1 |

It was observed from entry 1 and entry 2 that when the same catalyst was used, as the reaction time passes, the conversion rate was increased, and selectivity was slightly decreased, from which could be appreciated that a large amount of cyclic carbonate was present in the obtained product.

In entry 3, the most excellent selectivity was exhibited in the same reaction time.

It could be confirmed that entry 10 and entry 11 using aluminum metal complex had similar reactivity to the case of using iron metal complex; however, slightly decreased selectivity.

Therefore, it could be appreciated that when the metal complex of the present invention including the ligand including three phenolate donors bonded to the trisubstituted carbon and the salicylidene moiety is used as the catalyst for the reaction of carbon dioxide and alkylene oxide, the cyclic carbonate could be selectively prepared with high conversion rate to alkylene oxide.

[Example 12] Preparation of Cyclic Carbonate

Epoxide compounds 3-4 and 3-8 were prepared according to the method reported in document (Laserna, V.; Fiorani, G.; Whiteoak, C. J.; Martin, E.; Escudero-Adán, E.; Kleij, A. W. *Angew. Chem., Int. Ed.* 2014, 53, 10416).

The cyclic carbonation was performed as follows.

As shown in Table 2 below, the catalyst of the present invention, NBu$_4$Br and 1 g or 1 ml of epoxide were charged in 80 mL stainless steel reactor. Fe-1b of Example 2 was used as the catalyst, and NBu$_4$Br was used as the co-catalyst. The reactor was charged and discharged with 5 bar of $CO_2$ twice and finally charged with 10 bar of $CO_2$. The reactor was sealed, followed by stirring at 100° C. for predetermined time. After the reaction was completed, an aliquot of the reaction mixture was analyzed by $^1$H NMR spectroscopy using CDCl$_3$ as the solvent. The crude mixture was passed through the silica using 10:1 mixture of chloroform and ethyl acetate as an eluent to remove catalyst and ammonium salt. Solvent was removed under vacuum and target cyclic carbonate was obtained.

All of prepared cyclic carbonates 1-1 to 1-10 were cis-selective and the NMR spectra thereof were the same as the previously reported NMR spectra (Cyclic carbonates 1-1 to 1-3, 1-5, 1-6 to 1-10: Laserna, V.; Fiorani, G.; Whiteoak, C. J.; Martin, E.; Escudero-Adán, E.; Kleij, A. W. *Angew. Chem., Int. Ed.* 2014, 53, 10416; Cyclic carbonate 1-4: Orsini, F.; Sello, G.; Bestetti, G. *Tetrahedron: Asymmetry* 2001, 12, 2961.).

TABLE 2

| Entry | Epoxide compound | Catalyst used amount (mol %) | Co-catalyst used amount (mol %) | Reaction time (h) |
|---|---|---|---|---|
| 1 | 3-1 | 0.2 | 5.0 | 12 |
| 2 | 3-2 | 0.2 | 5.0 | 18 |
| 3 | 3-3 | 0.2 | 5.0 | 18 |
| 4 | 3-4 | 0.2 | 5.0 | 12 |
| 5 | 3-5 | 0.2 | 5.0 | 12 |
| 6 | 3-6 | 0.4 | 10.0 | 12 |
| 7 | 3-7 | 0.1 | 1.5 | 12 |
| 8 | 3-8 | 0.1 | 1.5 | 12 |
| 9 | 3-9 | 0.5 | 5.0 | 12 |
| 10 | 3-10 | 2.0 | 10.0 | 12 |

1) Compound 1-1:

Conversion rate 99%, Amount 1.25 g (91% Yield); $^1$H NMR (400 MHz, CDCl$_3$): δ 4.67-4.62 (m, 2H), 1.89-1.76 (m, 4H), 1.59-1.49 (m, 2H), 1.41-1.32 (m, 2H); $^{13}$C NMR (100 MHz, CDCl$_3$): 155.37, 75.75, 26.64, 19.04.

2) Compound 1-2:

Conversion rate 99%, Amount 1.14 g (90% Yield), mixture of diastereomers [see *Angew. Chem., Int. Ed.* 2014, 53, 10416.]; $^1$H NMR (400 MHz, CDCl$_3$): δ 5.76-5.66 (m, 2H), 5.05-4.96 (m, 4H), 4.78-4.60 (m, 4H), 2.34-2.09 (m, 5H), 2.03-1.94 (m, 1H), 1.82-1.51 (m, 5H), 1.38-1.27 (m, 2H), 1.21-1.11 (m, 1H); $^{13}$C NMR (100 MHz, CDCl$_3$): δ 155.19, 155.16, 140.95, 114.26, 113.96, 76.02, 75.66, 75.65, 75.15, 36.34, 33.89, 33.55, 31.67, 26.68, 25.79, 25.70, 25.06.

3) Compound 1-3:

Conversion rate 99%, Amount 0.94 g (77% Yield), mixture of diastereomers [see *Angew. Chem., Int. Ed.* 2014, 53, 10416.]; $^1$H NMR (400 MHz, CDCl$_3$): δ 4.76-4.73 (quint, 1H), 4.69-4.66 (quint, 1H), 4.65-4.58 (m, 2H), 3.53-3.51 (m, 18H), 2.30-2.04 (m, 4H), 1.80-1.76 (m, 1H), 1.70-1.47 (m, 4H), 1.41-1.07 (m, 8H), 0.97-0.87 (m, 1H), 0.63-0.58 (m, 4H); $^{13}$C NMR (100 MHz, CDCl$_3$): δ 155.31, 155.27, 76.45, 76.08, 76.07, 75.59, 50.64, 35.30, 33.97, 32.41, 32.10, 29.12, 28.84, 26.88, 26.03, 25.64, 25.05, 6.37, 6.25.

4) Compound 1-4:

Conversion rate 99%, Amount 1.42 g (94% Yield); $^1$H NMR (400 MHz, CDCl$_3$): δ 7.41-7.39 (dd, 1H), 7.36-7.28 (m, 2H), 7.21-7.19 (dd, 1H), 5.70-5.68 (d, 1H), 5.20-5.16 (quint, 1H), 3.00-2.92 (m, 1H), 2.72-2.66 (dt, 1H), 2.33-2.26 (m, 1H), 2.02-1.94 (m, 1H); $^{13}$C NMR (100 MHz, CDCl$_3$): δ 154.85, 138.30, 130.96, 129.93, 129.53, 128.84, 127.48, 75.78, 75.53, 27.27, 23.87.

5) Compound 1-5:

Conversion rate 99%, Amount 1.86 g (>99% Yield), mixture of diastereomers [see *Angew. Chem., Int. Ed.* 2014, 53, 10416.]; $^1$H NMR (400 MHz, CDCl$_3$): δ 4.92-4.69 (m, 2H), 4.63-4.16 (m, 3H), 2.44-2.35 (m, 1H), 2.21-1.86 (m, 2H), 1.82-1.69 (m, 2H), 1.67-1.24 (m, 2H); $^{13}$C NMR (100 MHz, CDCl$_3$): δ 154.75, 154.73, 154.67, 154.62, 154.58, 79.35, 79.14, 79.04, 79.02, 75.40, 75.23, 75.14, 75.04, 74.70, 74.64, 74.62, 67.61, 67.54, 67.37, 36.49, 36.36, 33.24, 33.09, 28.78, 28.45, 27.60, 26.39, 25.72, 25.10, 24.96, 21.00, 20.44, 19.64, 19.18.

6) Compound 1-6:

Conversion rate 99%, Amount 1.68 g (>99% Yield), mixture of diastereomers; $^1$H NMR (400 MHz, CDCl$_3$): δ 4.91-4.81 (m, 2H), 4.76-4.66 (m, 6H), 4.08-3.91 (m, 4H), 2.75-2.68 (m, 1H), 2.43-2.23 (m, 6H), 2.16-1.95 (m, 7H), 1.91-1.71 (m, 7H), 1.71-1.57 (4H), 1.49-1.07 (m, 3H); $^{13}$C NMR (100 MHz, CDCl$_3$): δ 174.02, 173.98, 173.21, 173.19, 154.93, 154.90, 154.77, 154.74, 154.72, 75.60, 75.55, 75.52, 75.19, 75.13, 74.99, 74.95, 74.75, 74.62, 68.20, 68.17, 68.06, 37.43, 37.41, 37.34, 37.24, 35.62, 32.17, 30.57, 30.51, 30.47, 29.43, 29.35, 29.32, 29.27, 29.25, 28.77, 28.74, 28.00, 26.17, 26.13, 25.42, 25.37, 25.34, 25.20, 25.17, 25.16, 25.12, 25.09, 22.37, 21.92, 21.87, 21.85, 21.44, 21.40; HRMS (ESI) m/z calculated for C$_{16}$H$_{20}$O$_8$ [M+Na$^+$]: 363.1056, found: 363.1075.

7) Compound 1-7:

Conversion rate 99%, Amount 1.36 g (95% Yield); $^1$H NMR (400 MHz, CDCl$_3$): δ 5.07-5.06 (m, 2H), 2.11-2.04 (m, 2H), 1.81-1.58 (m, 4H); $^{13}$C NMR (100 MHz, CDCl$^3$): δ 155.51, 81.92, 33.08, 21.53.

8) Compound 1-8:

Conversion rate 99%, Amount 1.40 g (94% Yield); $^1$H NMR (400 MHz, CDCl$_3$): δ 7.52-7.50 (dt, 1H), 7.44-7.40 (td, 1H), 7.37-7.31 (m, 2H), 6.01-5.99 (d, 1H), 5.46-5.42 (m, 1H), 3.40-3.39 (m, 1H); $^{13}$C NMR (100 MHz, CDCl$_3$): δ 154.84, 140.18, 136.58, 131.20, 128.37, 126.63, 125.74, 83.71, 79.89, 38.16.

9) Compound 1-9:

Conversion rate 99%, Amount 1.65 g (98% Yield); $^1$H NMR (400 MHz, CDCl$_3$): δ 5.20-5.19 (m, 2H), 4.24-4.21 (dd, 2H), 3.57-3.53 (m, 2H); $^{13}$C NMR (100 MHz, CDCl$_3$): δ 154.53, 80.18, 73.07.

10) Compound 1-10:

Conversion rate 99%, Amount 0.98 g (84% Yield). 0.9 ml of substrate was used. $^1$H NMR (400 MHz, CDCl$_3$): δ 4.84-4.78 (m, 2H), 1.99-1.86 (m, 4H), 7.84-1.74 (m 2H), 1.66-1.57 (m, 1H), 1.52-1.42 (m, 1H), 1.35-1.25 (m, 2H); $^{13}$C NMR (100 MHz, CDCl$_3$): δ 154.74, 79.91, 30.23, 30.00, 23.58.

The metal complex according to the present invention is a metal complex having a novel structure and consisting of a ligand having three phenolate donors bonded to a trisubstituted carbon and a salicylidene moiety, and a trivalent metal in Group 8 or Group 13, which has a pre-organized bite angle ideal to accommodate a 6-coordinate metal center, such that an enhanced rigidity effect of a ligand skeleton itself of the present invention is exhibited.

Therefore, the method for preparing cyclic carbonate from the reaction of alkylene oxide and carbon dioxide using the metal complex according to the present invention may increase selectivity by the pre-organized rigid metal complex so as to have the cis-binding site available for reducing the activation barrier of the reaction, thereby highly selectively preparing the cyclic carbonate with 90% or more of complete conversion rate to alkylene oxide.

Further, the cyclic carbonate according to the present invention may be used as a solvent or an additive constituting an electrolyte in a lithium secondary battery to exhibit more stable and excellent electrolyte performance.

What is claimed is:

1. A metal complex comprising a ligand represented by Chemical Formula 1 below and a trivalent metal in Group 8 or Group 13:

[Chemical Formula 1]

in Chemical Formula 1, R$^1$ is hydrogen, (C1-C20)alkyl or halogen; R$^2$ is hydrogen, (C1-C20)alkyl, (C1-C20)alkoxy, halogen or nitro.

2. The metal complex of claim 1, wherein the metal complex is represented by Chemical Formula 2 below:

[Chemical Formula 2]

in Chemical Formula 2, M is Fe or Al; R$^1$ is hydrogen, (C1-C20)alkyl or halogen; R$^2$ is hydrogen, (C1-C20)alkyl, (C1-C20)alkoxy, halogen or nitro.

3. The metal complex of claim 2, wherein the metal complex is selected from the following structures:

[Chemical Formula 4]

in Chemical Formulas 3 and 4, $R^{3a}$ and $R^{4a}$ are each independently hydrogen, (C1-C10)alkyl, halo(C1-C10)alkyl or (C6-C12)aryl, and $R^{3a}$ and $R^{4a}$ may be linked via (C3-C5)alkylene with or without a fused ring to form a ring, wherein the formed ring may be further substituted with vinyl, —(CH$_2$)$_a$SiR$^{11}$R$^{12}$R$^{13}$, oxiranyl or (7-oxa-bicyclo[4.1.0]heptane-3-yl)acetyl;

$R^{3b}$ and $R^{4b}$ are each independently hydrogen, (C1-C10)alkyl, halo(C1-C10)alkyl or (C6-C12)aryl, and $R^{3b}$ and $R^{4b}$ may be linked via (C3-C5)alkylene with or without a fused ring to form a ring, wherein the formed ring may be further substituted with vinyl, —(CH$_2$)$_a$SiR$^{11}$R$^{12}$R$^{13}$, 1,3-dioxolan-2-one-4-yl or (hexahydrobenzo[d][1,3]dioxol-2-one-5-yl)acetyl;

$R^{11}$ to $R^{13}$ are each independently (C1-C10)alkyl or (C1-C10)alkoxy; and a is an integer of 1 to 5.

6. The method of claim 4, wherein the metal complex catalyst has an amount of 0.1 to 2.0 mol % relative to the alkylene oxide.

7. The method of claim 4, wherein an ammonium co-catalyst or an amine-based co-catalyst is further included.

8. The method of claim 7, wherein the ammonium co-catalyst or the amine-based co-catalyst has an amount of 0.1 to 10.0 mol % relative to the alkylene oxide.

9. The method of claim 8, wherein the ammonium co-catalyst is selected from the group consisting of tetrabutylammonium bromide (NBu$_4$Br), tetramethylammonium bromide (NMe$_4$Br), tetraethylammonium tetrafluoroborate (NEt$_4$BF$_4$), tetrapropylammonium bromide (NPr$_4$Br), tetrahexylammonium chloride (N[(CH$_2$)$_5$CH$_3$]$_4$Cl), tetrapentylammonium bromide (N[(CH$_2$)$_4$CH$_3$]$_4$Br), tetraheptylammonium bromide (N[(CH$_2$)$_6$CH$_3$]$_4$Br), tetraoctylammonium bromide (N[CH$_2$)$_7$CH$_3$]$_4$Br), trimethyldodecylammonium chloride (CH$_3$(CH$_2$)$_{11}$N(CH$_3$)$_3$Cl), trimethyltetradecylammonium bromide (CH$_3$(CH$_2$)$_{13}$N(CH$_3$)$_3$Br), trimethylhexadecylammonium chloride (CH$_3$(CH$_2$)$_{15}$N(CH$_3$)$_3$Cl), methyltrioctylammonium chloride (CH$_3$N[(CH$_2$)$_7$CH$_3$]$_3$Cl), tetrabutylammonium fluoride (NBu$_4$F), tetrabutylammonium chloride (NBu$_4$Cl), tetrabutylammonium iodide (NBu$_4$I), 1-butyl-3-methylimidazolium bromide ([bmim]Br), 1-butyl-3-methylimidazolium chloride ([bmim]Cl), and bis(triphenylphosphine)iminium chloride ([((C$_6$H$_5$)$_3$P)$_2$N]Cl, PPNCl), and the amine-based co-catalyst is selected from the group consisting of triethylamine (Et$_3$N), 1,8-diazabicycloundec-7-ene (DBU), pyridine (C$_5$H$_5$N), and 4-dimethylaminopyridine (C$_7$H$_{10}$N$_2$, DMAP).

10. The method of claim 4, wherein a reaction temperature is 25 to 120° C., and a reaction pressure is 1 to 10 bar.

11. The method of claim 4, wherein the reaction is a neat reaction.

4. A method for preparing cyclic carbonate by reacting carbon dioxide with alkylene oxide using the metal complex of claim 1, as a catalyst.

5. The method of claim 4, wherein the alkylene oxide is represented by Chemical Formula 3 below, and the cyclic carbonate is represented by Chemical Formula 4 below:

[Chemical Formula 3]

* * * * *